United States Patent [19]

Newman et al.

[11] Patent Number: 5,668,012
[45] Date of Patent: Sep. 16, 1997

[54] PLATELET ENDOTHELIAL CELL ADHESION MOLECULE-1 PROMOTERS AND USES THEREOF

[75] Inventors: Peter J. Newman, Bayside; Richard J. Gumina; Nancy Kirshbaum, both of Milwaukee, all of Wis.

[73] Assignee: The Blood Center Research Foundation, Inc., Milwaukee, Wis.

[21] Appl. No.: 270,985

[22] Filed: Jul. 5, 1994

[51] Int. Cl.$^6$ .................... C12N 15/63; C07H 21/04
[52] U.S. Cl. .................... 435/320.1; 536/24.1
[58] Field of Search .................... 536/23.5, 24.1; 514/44; 435/69.1, 69.6

[56] References Cited

U.S. PATENT DOCUMENTS 5,264,554  11/1993  Newman .................... 530/387.1

OTHER PUBLICATIONS

Buck et al., C. R. Acad. Sci. Paris, Sciences de la vie/Life Sciences, vol. 316: pp. 849–859, Sep. 1993.
Newman et al., Science, vol. 247, pp. 1219–1222, 1990.
Albelda et al., J. Cell Bio., vol. 114, pp. 1059–1068, 1991.
Xie et al., PNAS, vol. 90, pp. 5569–5573, 1993.
Stockinger et al., J. Immunol., vol. 145, pp. 3889–3897, 1990.
Zehnder et al., JBC, vol. 267, pp. 5243–5249, 1992.
DeLisser et al., J. Cell Bio., vol. 124, pp. 195–203, Jan. 1994.
Gellicsen et al., Biotech Ado., vol. 10, pp. 179–189, 1992.

Primary Examiner—Donald E. Adams
Assistant Examiner—Stephen Gucker
Attorney, Agent, or Firm—Foley & Lardner

[57] ABSTRACT

Novel, substantially isolated isoforms of human platelet-endothelial cell adhesion molecule-1's, DNAs coding for transcripts that encode the novel isoforms and others, including a previously identified soluble isoform, methods of using such DNAs to make isoforms by expressing the DNA's, and promoter segments controlling transcription of human platelet-endothelial cell adhesion molecule-1 genes are provided. The novel isoforms differ from the complete human platelet-endothelial cell adhesion molecule-1's in lacking one or more segments near the C-terminus encoded by exons 10–15 of the genes for the full length molecules and arise in vivo from alternative splicing of the transcript from the genes.

4 Claims, No Drawings

PLATELET ENDOTHELIAL CELL ADHESION MOLECULE-1 PROMOTERS AND USES THEREOF

Work related to the invention described and claimed in this application was supported in part by grants from the United States National Institutes of Health. The United States Government has certain rights in the invention.

TECHNICAL FIELD

The present invention relates to a type of human protein molecule called "platelet-endothelial cell adhesion molecule-1," and often referred to simply as "PECAM-1." PECAM-1's are known to occur on the surfaces of platelets and leukocytes in blood as well as on the surfaces of endothelial cells in the walls of blood vessels. The proteins are involved in adhesion of these types of cells to one another and processes that involve such adhesion. As such, the proteins are involved in various conditions that involve the blood system, such as the inflammation associated with many injuries and diseases, atherosclerosis, and damage to blood vessels that results from angioplasty.

More particularly, the invention relates to certain novel, modified forms, known as "isoforms," of platelet-endothelial cell adhesion molecule-1's (PECAM-1's). These isoforms have been unexpectedly discovered in determining the detailed structure and organization of the gene for PECAM-1's. The invention also relates to novel DNAs that encode the isoforms of the invention, expression vectors that can be used to make the isoforms of the invention, and novel promoter segments that control expression in vivo of human platelet-endothelial cell adhesion molecule-1's from the genes that encode them.

BACKGROUND OF THE INVENTION

Full-length, mature platelet-endothelial cell adhesion molecule-1's (PECAM-1's) are glycosylated proteins with 711 amino acids and a molecular weight of approximately 130 kilodaltons. The proteins are members of the immunoglobulin superfamily. They are expressed on platelets, at the intercellular junctions of resting endothelial cells, and on circulating monocytes, granulocytes, and certain subsets of T-cells. Newman et al. (I) (1990) Science 247, 1219–1222; Muller, et al. (I) (1989) J. Exp. Med. 170, 399–414; Albelda, et al. (I) (1990) J. Cell. Biol. 110, 1227–1237; Ashman and Aylett (1991) Tissue Antigens 38, 208–212.

From a molecular cloning study, it is known that PECAM-1's have 6 extracellular Ig-like domains, a short transmembrane region, and a relatively long 118 amino acid (aa) cytoplasmic tail containing multiple potential sites for phosphorylation, lipid modification, and other post-translational modifications. Newman et al. (I), supra, and Newman, U.S. Pat. No. 5,264,554 (the '554 Patent), which is incorporated in its entirety herein by reference.

Three full-length, mature PECAM-1's have been found. One of these, designated herein as "form 1," has the amino acid sequence shown in FIG. 1 of the '554 Patent. The amino acid sequences of the other two are the same as the amino acid sequence of form 1 except that in one of them, designated herein as "form 2," which is the one for which portions of the amino acid sequence are provided in SEQ ID NO:3 through SEQ ID NO:11 hereinbelow, there is an asparagine rather than a serine at amino acid position 536, due to a change from a 2'-deoxyguanylate to a 2'-deoxyadenylate at nucleotide position 1829 in the cDNA sequence in FIG. 1 of the '554 Patent (which corresponds to nucleotide position 196 in SEQ ID NO:3 hereinbelow), Stockinger et al. (1990) J. Immunol. 145, 3889–3897, and in the other, designated herein as "form 2," there is an isoleucine rather than an asparagine at amino acid position 88 (resulting from a change from a 2'-deoxyadenylate to a 2'-deoxythymidylate at nucleotide position 485 in the cDNA of FIG. 1 of the '554 Patent), an aspartic acid rather than an asparagine at amino acid position 124 (resulting from a change from a 2'-deoxyadenylate to a 2'-deoxyguanylate at nucleotide position 553 in the cDNA of FIG. 1 of the '554 Patent), a methionine rather than an isoleucine at amino acid position 348 (resulting from a change from a 2'-deoxyadenylate to a 2'-deoxyguanylate at nucleotide position 1266 in the cDNA of FIG. 1 of the '554 Patent), and a valine rather than an aspartic acid at amino acid position 364 (resulting from a change from a 2'-deoxyadenylate to a 2'-deoxythymidylate at position 1313 in the cDNA of FIG. 1 of the '554 Patent), Zehnder et al. (1992) J. Biol. Chem. 267, 5243–5249. In addition, at several nucleotide positions in the cDNA's for PECAM-1's, silent substitutions (substitutions not resulting in amino acid changes) have been found. With reference to the cDNA sequence in FIG. 1 of the '554 Patent, such silent substitutions have been found at positions 514, 1593, and 2149 (which corresponds to nucleotide position 38 in SEQ ID NO:7 hereinbelow) in the amino acid-coding region and, in the 3'-untranslated region, position 2416 (which corresponds to nucleotide position 108 in SEQ ID NO:11 hereinbelow). See Newman et al. (I), supra; Stockinger et al., supra; Zehnder et al., supra; and the '554 Patent. Apparently, then, a number of nearly identical alleles of PECAM-1 genomic DNA exist in the human gene pool.

No polymorph of a PECAM-1 has been found with an amino acid substitution in the cytoplasmic domain, the amino acids at positions 594–711.

A soluble form of a PECAM-1, with a molecular weight between about 6,000 and 9,000 daltons less than that of a full length, mature PECAM-1 has been identified. Goldberger et al., Blood 80, 266a (1992).

PECAM-1's are important mediators of platelet-platelet, platelet-leukocyte, and platelet-endothelial cell interactions involved in platelet aggregation, development of atherosclerotic plaque, and development of thrombi as a result of vascular trauma, as may be caused, for example, by angioplasty or similar processes. PECAM-1's are also involved in leukocyte-endothelial cell interactions involved in processes such as transendothelial cell migration and related phenomena such as inflammation. Muller et al. (II) (1993) J. Exp. Med. 178, 449–460 and Vaporciyan et al. (1993) Science 262, 1580–1582 describe the use of PECAM-1 specific antibodies to interfere with neutrophil recruitment and transendothelial migration. The mechanisms by which PECAM-1's mediate these cellular interactions are complex, as PECAM-1's can interact both homophilically (a PECAM-1 molecule binding to a PECAM-1 molecule), Albelda et al. (II) (1991) J. Cell. Biol. 114, 1059–1068, as well as heterophilically (a PECAM-1 molecule binding to a molecule other than a PECAM-1 molecule), Muller et al. (III) (1992) J. Exp. Med. 175, 1401–1404 and DeLisser et al. (1993) J. Biol. Chem. 268, 16037–16046, to carry out its adhesive functions.

The cytoplasmic domain of a PECAM-1 molecule is the 118 C-terminal amino acids, amino acids 594–711, in the mature molecule. This domain plays an important role in regulating the adhesive properties of a PECAM-1. Removal of C-terminal portions in recombinant PECAM-1 constructs has been found to convert the molecule from heterophillic to homophilic ligand-binding specificity, DeLisser et al. (II) (1994) J. Cell. Biol. 124, 195–203. The cytoplasmic domain has sites for phosphorylation and lipid modification and interacts with the cytoskeleton, Newman et al. (II) (1992) J. Cell. Biol. 119, 239–246 (1992); Zehnder et al., supra. Modifications in the cytoplasmic domain affect not only the adhesive properties of a PECAM-1's extracellular domain but also its subcellular distribution, interactions with intracellular signalling molecules, and ability to participate in intercellular signal transduction.

SUMMARY OF THE INVENTION

The present invention rests on a study of the organization and structure of the human genomic DNA, from the short arm of chromosome 17, from which a human platelet-endothelial cell adhesion molecule-1 ("PECAM-1") is expressed.

In this study, it has been discovered that the gene for the PECAM-1 includes 16 exons. Unexpectedly, it has been discovered that an unusually high number of exons, 7 of them, exons 10–16, are involved in coding for the "cytoplasmic tail" of the PECAM-1 molecule and that alternative forms ("isoforms") of the PECAM-1, with cytoplasmic tails that differ in amino acid sequence, arise from differential splicing of the transcript of the PECAM-1 gene. This differential splicing results in exclusion, from the mRNA that is translated to make the protein, of the portions of the transcript corresponding to one or more of exons 10–15. The resulting, different mRNAs encode PECAM-1 isoforms with different cytoplasmic tails. Thus, the invention provides substantially isolated isoforms of PECAM-1 that differ in their cytoplasmic tails.

In this study it also has been found that exon 9 in the PECAM-1 gene provides the part of the transcript that, if present in the mRNA, provides the domain of the protein that anchors it in the cell membrane. The transcript corresponding to exon 9 can also be excluded, alone or together with one or more of the transcripts corresponding to exons 10–15, by differential splicing from the mRNA that encodes an isoform of a PECAM-1. Indeed, it has been discovered as part of this invention that the soluble PECAM-1 reported by Goldberger et al., supra, results from an mRNA that lacks the transcript coded for by exon 9.

Other isoforms of the invention may be soluble because they lack a segment of amino acids that is required to anchor PECAM-1 or its isoforms in cell membranes. These other isoforms include those which are encoded from an mRNA which lacks not only a part of the transcript of the PECAM-1 gene corresponding to one or more of exons 10–15 of the gene but also the part of the transcript corresponding to exon 9 or at least bases 44–100 of that exon as shown in SEQ ID NO:4 below. The isoforms corresponding to the lack in the mRNA encoding the isoforms of a part of the transcript corresponding to one or more of exons 10–15 of the gene and exon 9 of the gene can arise from differential splicing. The isoforms corresponding to the lack in the mRNA encoding the isoforms of a part of the transcript corresponding to one or more of exons 10–15 of the gene and bases 44–100, as shown in SEQ ID NO:4, of exon 9 of the gene can, like all of the isoforms of the invention, be made by expression of a cDNA with a sequence that is transcribed into an mRNA that encodes the isoform.

Further, in the study that underlies the invention, DNA segments ("promoter segments") have been discovered that act as promoters for initiation and control of transcription of the gene for the PECAM-1. These promoter segments permit transcription of any DNA, to which they are joined operably for initiation of transcription, substantially only in cells of the vasculature and, particularly, vascular endothelial cells, leucocytes, or platelet precursors (e.g., megakaryocytes) in which PECAM-1 is normally expressed. Thus, the promoter segments are useful for limiting to these types of cells expression of a gene to produce a protein of interest (including possibly a full-length PECAM-1 itself) or transcription of a DNA to produce an anti-sense RNA of interest.

Other aspects of the invention, described more fully below in the specification and claims, flow from the discovery of the isoforms of the invention, DNA segments that code for transcripts that encode the isoforms, and the promoter segments of the invention.

BRIEF DESCRIPTION OF THE SEQUENCES PROVIDED IN THE SEQUENCE LISTING

SEQ ID NO:1 is the sequence of the first (i.e., the 5'-most or furthest "up-stream") 492 base pairs determined in the study that underlies the present invention of the gene for a human platelet-endothelial cell adhesion molecule-1. The 492 base pairs immediately preceded what was determined in the study to be the most frequently used first (i.e., the 5'-most or furthest "up-stream") base pair of the first exon of the gene. The DNA segment with the sequence of SEQ ID NO:1 is a promoter segment of the invention.

SEQ ID NO:2 is the sequence of base pairs 259–492 from SEQ ID NO:1. Several subsegments of the segment with the sequence of SEQ ID NO:2 have sequences characteristic of cis-acting elements that occur in promoters. Thus, base pairs 1–7 of SEQ ID NO:2 have the sequence of a segment that occurs in promoters associated with acute phase reactants; base pairs 14–22 of SEQ ID NO:2 have the sequence of an inverted NF-κB site, which occurs in promoters whose transcriptional activity is regulated by cytokines; base pairs 46–52 and 187–191 of SEQ ID NO:2 have 725 sequences of ets sites, which are recognized by the polyomavirus enhancer A-binding protein; base pairs 207–216 have a sequence of an ets site combined with a consensus sequence of a GATA element (5'-AGATA), which is known to be involved in regulation of gene expression in cells of the megakaryocytic lineage; and base pairs 200–223 have a RNA polymerase II transcription initiator consensus sequence similar to that found in other promoters which, like the segment with the sequence of SEQ ID NO:2, lack the 5'-TATA recognition sequence for that polymerase. The segment with the sequence of SEQ ID NO:2 is a subsegment that has transcription-control activity of the segment with the sequence of SEQ ID NO:1.

SEQ ID NO:3 is the sequence of exon 8 together with the sequence of the first (i.e., the 5'-most or most "upstream") twenty bases of the intron that immediately follows (i.e., is 3'-from or "downstream" from) exon 8 in the gene examined in the study that underlies the present invention.

SEQ ID NO:4 is the sequence of exon 9 together with the sequence of the last (i.e., the 3'-most or most "downstream") twenty bases of the intron that immediately precedes (i.e., is 5'-from or "upstream" from) exon 9 and the sequence of the first twenty bases of the intron that immediately follows exon 9 in the gene examined in the study that underlies the present invention. Exon 9 encodes the segment of a platelet-endothelial cell adhesion molecule-1, or an isoform thereof, that is termed the "transmembrane domain." Expression of such an isoform from a DNA segment from which a segment of exon 9 that comprises the segment from base 44 to base 100 as shown in SEQ ID NO:4 has been deleted results in a soluble, rather than a membrane-bound, polypeptide. Amino acids 1-8 and 28-36 shown in SEQ ID NO:4 are thought to be involved in anchoring of polypeptide to the cell or platelet membrane but, unlike amino acids 9-27, do not need to be absent from a polypeptide for the polypeptide to be soluble. Amino acids 9-27 shown in SEQ ID NO:4 correspond to amino acids 575-593 of the platelet-endothelial cell adhesion molecule-1 for which the sequence is shown in FIG. 1 of U.S. Pat. No. 5,264,554 (the '554 Patent).

SEQ ID NO:5 is the sequence of exon 10 together with the sequence of the last twenty bases of the intron that immediately precedes exon 10 and the sequence of the first twenty bases of the intron that immediately follows exon 10 in the gene examined in the study that underlies the present invention.

SEQ ID NO:6 is the sequence of exon 11 together with the sequence of the last twenty bases of the intron that immediately precedes exon 11 and the sequence of the first twenty bases of the intron that immediately follows exon 11 in the gene examined in the study that underlies the present invention.

SEQ ID NO:7 is the sequence of exon 12 together with the sequence of the last twenty bases of the intron that immediately precedes exon 12 and the sequence of the first twenty bases of the intron that immediately follows exon 12 in the gene examined in the study that underlies the present invention.

SEQ ID NO:8 is the sequence of exon 13 together with the sequence of the last twenty bases of the intron that immediately precedes exon 13 and the sequence of the first twenty bases of the intron that immediately follows exon 13 in the gene examined in the study that underlies the present invention.

SEQ ID NO:9 is the sequence of exon 14 together with the sequence of the last twenty bases of the intron that immediately precedes exon 10 and the sequence of the first twenty bases of the intron that immediately follows exon 14 in the gene examined in the study that underlies the present invention.

SEQ ID NO:10 is the sequence of exon 15 together with the sequence of the last twenty bases of the intron that immediately precedes exon 15 and the sequence of the first twenty bases of the intron that immediately follows exon 15 in the gene examined in the study that underlies the present invention.

SEQ ID NO:11 is the sequence of the 3'-most (most "downstream") 921 bases determined in the study that underlies the present invention of the gene for a human platelet-endothelial cell adhesion molecule-1. The sequence of the first twenty bases in SEQ ID NO:11 is the sequence of the last twenty bases of the intron that immediately precedes exon 16 of that gene. The sequence of the last 901 bases in SEQ ID NO:11 is the sequence of the first (5'-most) 901 base pairs of that exon 16. Of these 901 base pairs, 871 are 3'-from the triplet corresponding to the stop codon in the mRNA encoding the full length protein and any isoform thereof for which the reading frame of the mRNA is not altered by lack of an exon. There is no 5'-AATAAA primary consensus polyadenylation signal sequence among these 871 base pairs. However, two secondary consensus polyadenylation signal sequences occur at bases 380-385 and bases 536-541 in SEQ ID NO:11. Base 249 in SEQ ID NO:11 corresponds to base 2557 in the platelet-endothelial cell adhesion molecule-encoding cDNA provided in FIG. 1 of the '554 Patent.

SEQ ID NO:3 through SEQ ID NO:11 also show the amino acid sequences encoded by the portions of those sequences that correspond to exons. In cases where an intron interrupts the triplet corresponding to a codon for an amino acid, the encoded amino acid is shown with the exon sequence that includes two of the three bases of the triplet.

SEQ ID NO:12, SEQ ID NO:13, SEQ ID NO:14, and SEQ ID NO:15 are the sequences of primers used in the study that underlies the present invention. SEQ ID NO:12 is complementary to the sequence of bases 100-141 of the platelet-endothelial cell adhesion molecule-encoding cDNA provided in FIG. 1 of the '554 Patent. SEQ ID NO:13 is complementary to the sequence of bases 2465-2482 of that cDNA sequence in FIG. 1 of the '554 Patent. SEQ ID NO:14 has the same sequence as bases 2085-2102 of that cDNA sequence in FIG. 1 of the '554 Patent. Finally, SEQ ID NO:15 has the sequence complementary to that of bases 2324-2343 of that cDNA sequence in FIG. 1 of the '554 Patent.

SEQ ID NO:16, SEQ ID NO:17, SEQ ID NO:18, SEQ ID NO:19, SEQ ID NO:20, and SEQ ID NO:21 are sequences of primers used to construct, from cDNAs encoding isoforms of the invention which have a segment corresponding to bases 44-100 of exon 9 as shown in SEQ ID NO:4, cDNAs which lack that segment and therefore can be used to make soluble isoforms of the invention. SEQ ID NO:16 is the sequence of bases 1602-1621 of the cDNA for which the sequence is provided in FIG. 1 of the '554 Patent. The sequence of the 5'-most 16 bases in SEQ ID NO:17 is the sequence complementary to that of bases 1929-1944 in the cDNA for which the sequence is provided in FIG. 1 of the '554 Patent, and the sequence of the 3'-most 18 bases in SEQ ID NO:17 is the sequence complementary to that of bases 2002-2019 in that cDNA. SEQ ID NO:18 is complementary to SEQ ID NO:17. SEQ ID NO:19 is the sequence complementary to that of bases 2465-2482. SEQ ID NO:20 is the same as that of bases 1754-1773, and SEQ ID NO:21 is the sequence complementary to that of bases 2324-2343 in the cDNA for which the sequence is provided in FIG. 1 of the '554 Patent.

DETAILED DESCRIPTION OF THE INVENTION

In one of its aspects, the invention is a substantially isolated isoform of a human platelet-endothelial cell adhesion molecule-1, which is full-length and mature, wherein the isoform has the sequence of amino acids that results from translation of the mRNA that is the same as a mRNA that is translated to make the human platelet-endothelial cell adhesion molecule-1 except that the mRNA that is translated to make the isoform lacks one or more of the mRNA segments corresponding to exons 10-15 of the gene for the human platelet-endothelial cell adhesion molecule-1 and optionally also lacks the mRNA segment corresponding to exon 9 in its entirety of said gene or any continuous segment of said exon 9 that comprises base pairs 44-100 as shown in SEQ ID NO:4 and has a number of base pairs that is evenly divisible by 3.

In another of its aspects, the invention is a DNA segment which codes for a transcript for an isoform of a human platelet-endothelial cell adhesion molecule-1, which is full-length, wherein the isoform has the sequence of amino acids that results from translation of the mRNA that is the same as a mRNA that is translated to make the human platelet-endothelial cell adhesion molecule-1 except that the mRNA that is translated to make the isoform lacks one or more of the mRNA segments corresponding to exons 9–15 of the gene for the human platelet-endothelial cell adhesion molecule-1 and, if said mRNA that is translated to make the isoform does not lack the entire segment corresponding to exon 9 of said gene, said mRNA that is translated to make the isoform optionally lacks the mRNA segment corresponding to any continuous subsegment of said exon 9 that comprises base pairs 44–100 as shown in SEQ ID NO:4 and has a number of base pairs that is evenly divisible by 3.

The DNA segments of the invention may be included in expression vectors operably for expression of isoforms, for which the DNA segments of the invention code for transcripts, in cells, in culture (including cultures maintained in vivo in animals, such as in the peritoneal cavities of mice or rats) or in vivo in humans. Preferred expression vectors would provide expression of isoforms of the invention in mammalian cells in culture or in cells of the vasculature in vivo in humans. A promoter segment of the invention (see below) may be employed to drive expression specifically in cells of the vasculature in humans. Thus, a DNA segment of the invention may be used to make, in cells in culture or otherwise as just indicated for the expression vectors, the isoform, for which the segment codes for a transcript, in a method that comprises expressing the DNA segment; and the invention encompasses such methods of use of the DNA segments of the invention.

The invention also encompasses such expression vectors, cells transformed with such vectors, cultures of such cells, and methods of making isoforms of the invention by expression, in cells in culture or otherwise, from expression vectors of the invention.

Still further the invention entails a promoter segment which (i) has a sequence that is substantially the same as SEQ ID NO:1 or any subsequence thereof, such as, for example, SEQ ID NO:2, that is transcription-control-active with respect to (i.e., capable of initiating or controlling transcription of) a DNA segment operably joined thereto for transcription and (ii) is not on the long arm of a human chromosome 17 if the promoter segment is positioned immediately 5' to the gene for a human platelet-endothelial cell adhesion molecule-1.

The invention still further entails the method of using a promoter segment of the invention to control transcription of a DNA segment to make an anti-sense RNA, or control expression of a gene to make a protein (including possibly, but not limited to, a full-length PECAM), in cells of the vasculature, especially vascular endothelial cells, leukocytes, and platelet-precursors (e.g., megakaryocytes) in which PECAM-1 is naturally expressed.

By "substantially isolated" with respect to the isoforms of the invention is meant "separated from the environment in which the isoform occurs in nature." Thus, among other possibilities, isoforms in cells in culture, isoforms in living humans in cells in which the isoforms do not occur naturally or occur naturally but at a different concentration, isoforms on chromatographic or electrophoretic gels, in liposomes, or in solution would be "substantially isolated." Certainly, isoforms in aqueous solution, such as a solution that is pharmaceutically acceptable for administration to an human by injection or otherwise, would be "substantially isolated."

In such pharmaceutically acceptable solutions, an isoform of the invention may be present at a concentration between about 10 nM and the lower of about 50 µM and the isoform's solubility in the solution. A concentration of at least about 50 nM and more usually at least about 1 µM will be used.

An isoform of the invention which includes the transmembrane domain (the segment of amino acids at positions 575–593 in FIG. 1 of the '554 Patent, which corresponds to amino acids 9–27 in SEQ ID NO:4) is advantageously incorporated into a liposome for suspension in solution and administration to a human, typically by intravenous or intraarterial infusion or injection of such a solution.

Reference to a "mature" isoform or other protein means that the protein does not have a signal peptide.

Reference to a "full length" platelet-endothelial cell adhesion molecule-1 means one that has the entire sequence of amino acids that the molecule has naturally. In the case of the three human forms of these molecules that are now known, this "full length" sequence has 711 amino acids in the "mature" molecules and 738 amino acids in the "full length" molecules with the signal peptide.

A "cDNA segment" that codes for an RNA means the a DNA segment that can be transcribed to make the RNA but has no introns. Unless otherwise qualified, a "cDNA" or a "cDNA segment" is double-stranded. A cDNA segment for a protein or a polypeptide means a DNA segment that has no introns and that can be transcribed into an RNA that, in turn, can be translated to make the protein or polypeptide (i.e., "encodes" the protein or polypeptide).

A "gene" for a protein or polypeptide means (1) a segment of a genomic DNA for the protein or polypeptide, which segment is transcribed into RNA but may have introns, where the RNA, after processing to remove segments corresponding to introns, is capable of being translated into the protein or polypeptide or (2) segment that is not a cDNA segment but that differs from that specified in part (1) of this paragraph only by one or more nucleotide substitutions, deletions, and additions that, in aggregate, are silent. Such substitutions, deletions, and additions are "silent," in aggregate, if the segment with them is transcribed into an RNA that, after processing to remove segments corresponding to introns, is capable of being translated into the same protein or polypeptide.

A "genomic DNA" means DNA that is part of a chromosome and may include not only a "gene" (a segment that is transcribed) but also segments that are not transcribed, such as promoter segments, that control transcription of genes that may be part of the DNA.

All amino acids referred to in this specification, except the non-enantiomorphic glycine, are L-amino acids. An amino acid may be referred to using the standard three-letter designation, as indicated in the following Table I.

TABLE I

Designations for Amino Acids

| Amino Acid | Three-Letter Designation |
|---|---|
| L- alanine | Ala |
| L- arginine | Arg |
| L- asparagine | Asn |
| L- aspartic acid | Asp |
| L- cysteine | Cys |
| L- glutamic acid | Glu |
| L- glutamine | Gln |
| glycine | Gly |
| L- histidine | His |
| L- isoleucine | Ile |
| L- leucine | Leu |
| L- lysine | Lys |
| L- methionine | Met |
| L- phenylalanine | Phe |
| L- proline | Pro |
| L- serine | Ser |
| L- threonine | Thr |

TABLE I-continued

Designations for Amino Acids

| Amino Acid | Three-Letter Designation |
|---|---|
| L- tryptophan | Trp |
| L- tyrosine | Tyr |
| L- valine | Val |

Peptide or polypeptide sequences are written and numbered from the amino-terminal amino acid to the carboxy-terminal amino acid.

The standard, one-letter codes "A," "C," "G," and "T" are used herein for the nucleotides adenylate, cytidylate, guanylate, and thymidylate, respectively. The skilled will understand that, in DNAs, the nucleotides are 2'-deoxyribonucleotide-5'-phosphates (or, at the 5'-end, triphosphates) while, in RNAs, the nucleotides are ribonucleotide-5'-phosphates (or, at the 5'-end, triphosphates) and uridylate (U) occurs in place of T. "N" means any one of the four nucleotides. "dNTP" means any one of the four 2'-deoxyribonucleoside-5'-triphosphates Oligonucleotide or polynucleotide sequences are written from the 5'-end to the 3'-end.

A promoter segment is "substantially the same" as one of specified sequence if its sequence differs at one or more positions from that of the segment of specified sequence but, in a mammalian cell of the vasculature, such as an human umbilical vein endothelial cell ("HUVEC," Newman et al. (III) (1986) J. Cell. Biol. 103, 81–86) or an ECV304 cell (ATCC CRL-1998), the segment initiates transcription at a rate that is at least 10% and more preferably at least 50% of the rate of initiation of transcription by the segment of specified sequence, in a standard assay for promoter activity. See, e.g., Sections 9.6 and 9.7 of Current Protocols in Molecular Biology, edited by Ausubel et al., Current Protocols, a joint venture between Greene Publishing Associates, Inc. and John Wiley & Sons, Inc. (1994).

Positioning a promoter segment "operably for transcription" with respect to a segment to be transcribed is straightforward for a person of ordinary skill. It means orienting and positioning the promoter segment in a larger DNA segment that comprises both the promoter segment and the segment to be transcribed under the control of the promoter segment such that, in a cell in which the promoter segment is effective in initiating transcription, the segment to be transcribed is in fact transcribed in a transcription process that is initiated from the promoter segment.

It would be routine for a person of skill to determine, by methods well known in the art, subsegments of a promoter segment of the invention that remain transcription-control-active. Subsegments are prepared by any of numerous, standard, techniques. See, for example. Chapter 8 of Current Protocols in Molecular Biology, supra. Testing for transcription-control-activity of a subsegment can be by any standard assay for promoter activity, as indicated above, in Sections 9.6 and 9.7 of Current Protocols in Molecular Biology, supra.

The promoter segments and subsegments of the invention may be joined operatively for transcription to genes, or preferably cDNAs, for proteins of interest to be expressed in cells of the vasculature. These proteins may include not only PECAM-1's or isoforms thereof but also proteins such as adenosine deaminase, to treat immune deficiency due to deficiency of that enzyme, or Factor IX, to treat the form of hemophilia due to lack of that factor. The resulting constructs may then be transformed into cells of the vasculature, such as endothelial cells, leukocytes, or platelet precursor cells, by standard transformation techniques, including without limitation retroviral mediated transformation. The transformed cells, in the person to be treated, will then produce the protein of interest.

The promoter segments and subsegments of the invention may be joined operatively for transcription to DNAs that are oriented with respect to the direction of transcription from the promoter segment or subsegment to yield, on transcription, anti-sense RNAs in cells of the vasculature. As understood by the skilled, such an anti-sense RNA, by hybridizing in the cell in which it is made to a DNA or RNA segment that is complementary in sequence, blocks the function of the DNA or RNA segment and thereby eliminates or inhibits expression of a gene which depends on such function. For example, an anti-sense RNA might inhibit expression of a gene for a protein by hybridizing to all or part of the mRNA that is translated into the protein and thereby blocking translation of the mRNA. A promoter segment, or subsegment thereof, of the invention might be used to transcribe a cDNA, for all or part of a PECAM-1, which cDNA is oriented, with respect to the direction of transcription from the promoter segment or subsegment, to produce an RNA with the sequence complementary to that of all or part, respectively, of mRNA that is translated to yield the PECAM-1. The quantity of PECAM-1 produced by the cell so transformed would be reduced or eliminated. This would be of therapeutic advantage in treating conditions, such as inflammation, dependent on transendothelial migration of leukocytes, or arterial occlusion, dependent on binding among platelets and cells that naturally have PECAM-1's on their surfaces, in which interactions of PECAM-1 molecules with other PECAM-1 molecules or with other cell-surface proteins are implicated.

To make isoforms of the invention, reference is made to the description in the '554 Patent. The isoforms which are encoded by mRNAs that lack the entire segment(s) corresponding to one or more exons, other than exon 9, occur naturally, at low levels, in membranes of cells of the vasculature and so may be isolated from such cells by straightforward modifications of the procedures described in the '554 Patent for obtaining PECAM-1 from cells in recoverable form. In these procedures for isolating isoforms from cells, antibodies may be employed that are obtained using as antigen PECAM-1 isoforms produced in large amounts from cells in culture transformed with expression vectors to make the isoforms.

Isoforms of the invention which lack the amino acid segment corresponding to exon 9, or the amino acid segment corresponding to amino acids 9–27 of that segment corresponding to exon 9, as shown in SEQ ID NO:4, are soluble. Those lacking the segment corresponding to exon 9 occur naturally in the blood serum and may be isolated therefrom by standard techniques, again alternatively employing antibodies that can be developed using as antigen the corresponding PECAM-1 isoforms, respectively, produced in large amounts from cells in culture transformed with expression vectors to make the isoforms.

The isoforms of the invention, and the isoforms which lack the entire amino acid segment corresponding to exon 9, are preferably made by using DNA segments of the invention as part of expression vectors and culturing cells that have been transformed with the expression vectors to make the isoforms by expressing the isoform-encoding DNAs of the invention. In this regard, with respect to preparing expression vectors to make the isoforms in bacteria, yeast, or mammalian cells, reference may be had not only to the '554 Patent but also standard works relating to such vectors, including, for example, Current Protocols in Molecular Biology, supra. Preparing the isoforms in mammalian cells, and particularly human cells, in culture, such that their glycosylation will be similar to that of the naturally occurring forms, would be preferred. For expression in mammalian cells, cells developed using a system involving amplification of copy number of the gene of interest using a dihydrofolate/reductase-methothrexate system are preferred. See Chapter 16, and especially Section 16.14, of Current Protocols in Molecular Biology, supra.

The isoforms of the invention may be employed as described for PECAM-1 in the '554 Patent.

Thus, the isoforms of the invention can be used, for example, to make antibodies, and preferably monoclonal antibodies, for various diagnostic and therapeutic uses.

Isoforms of the invention are to be administered to humans under the guidance of a physician.

The soluble isoforms of the invention, or provided with the DNAs of the invention, can be administered to humans in a single dose, by a single intravenous or intraarterial injection or by intravenous or intraarterial infusion over a period of time of between about 1 minute and 10 hours, in an aqueous vehicle that is pharmaceutically acceptable, of between about 0.05 mg/kg and about 5 mg/kg of body weight of the recipient to relieve inflammation due to leukocyte transmigration arising in many situations, including arthritis, bee stings, spider bites, sepsis, anaphylactic shock, and other conditions, or to inhibit arterial occlusions associated with atherosclerosis or vascular trauma due to angioplasty or the like.

The actual dosage regimen will vary from individual to individual depending on, among other factors, the purpose for which an isoform is being administered and the medical condition of the individual.

Isoforms of the invention which are not soluble can be combined with liposomes and the resulting liposomes administered to have effects similar to those of the soluble isoforms.

The invention will now be described in additional detail in the following examples, which are provided for purposes of illustrating and demonstrating the invention but not limiting it.

EXAMPLE 1

This Example provides a description of a study of the structure and organization of genomic DNA for a PECAM-1 and a determination of sequences of cDNAs that code for mRNAs that encode various isoforms of PECAM-1's.

Two human genomic libraries, constructed from Sau3AI partially digested peripheral blood leukocyte DNA cloned into lambda phage vectors, were screened and yielded the majority of the PECAM-1 gene. The first library, in λEMBL3, was obtained from Clontech Laboratories (Palo Alto, Calif., USA). The second library in λGEM-11 came from Novagen (Madison, Wis., USA).

Library screening was carried out by plaque-lift hybridization (Sambrook et al. (1989) *Molecular Cloning: A Laboratory Manual*, Cold Spring Harbor Laboratory Press, Cold Spring Harbor, N.Y.) using full-length or partial PECAM-1 cDNA probes $^{32}$P-labeled by random priming with [α-$^{32}$P] dCTP (DuPont, New England Nuclear, Boston, Mass., USA) and an oligolabeling kit (Pharmacia, Piscataway, N.J., USA) (Feinberg and Vogelstein (1983) Anal. Biochem. 132, 6–13). Positive clones were plaque-purified and phage DNA was isolated following standard procedures (Sambrook et al., supra) for characterization of the genomic insert.

A genomic clone of approximately 45 kb containing a portion of the PECAM-1 genomic DNA was derived from a P1 phagemid library (clone #530, Genome Systems, St. Louis, Mo., USA) by PCR-based screening using PECAM-1-specific primers.

All inserts were characterized by restriction endonuclease mapping. Restriction fragments containing exons were identified by Southern blot hybridization of restriction endonuclease digests with $^{32}$P-labeled PECAM cDNA probes. Restriction endonuclease digests of genomic clone DNA, separated by 1% agarose gel electrophoresis, were transferred to nylon membranes (Boehringer Mannheim Biochemicals, Indianapolis, Ind., USA or Micron Separations, Inc., Westborough, Mass., USA) by vacuum transfer. Prehybridization and hybridization were carried out at 68° C. in 5× Denhardt's solution (Sambrook et al., supra), 6× SSC (1× SSC: 0.15M sodium chloride, 0.015M sodium citrate, pH 7), 5 mM disodium ethylenediamine tetraacetic acid (EDTA), 10 mM sodium phosphate, pH 7, 1% sodium dodecyl sulfate (SDS), 50 µg/ml herring sperm DNA. Labeled probe was added at 2–3×10$^6$ cpm/ml and allowed to hybridize for 18 hr. The membranes were washed at 68° C.: twice in 2× SSC, 0.1% SDS, once in 0.5× SSC, 0.1% SDS, and twice in 0.1× SSC, 0.1% SDS; each wash lasted 30 min.

In certain instances, exons were too small to be detected by hybridization of double-stranded DNA probes. Therefore, when appropriate, oligonucleotide hybridization was performed. Synthetic oligonucleotides derived from the sequence of PECAM-1 cDNA (see the '554 Patent) were $^{32}$P-labeled with [γ-$^{32}$P] dATP (DuPont, New England Nuclear) and T4 polynucleotide kinase (Promega, Madison, Wis., USA, or New England Biolabs, Boston, Mass., USA). Membranes were prehybridized in 5× Denhardt's solution, 6× SSC, 5 mM EDTA, 10 mM sodium phosphate, pH 7, 1% SDS. Hybridizations were carried out at 50° C. for at least 18 hr. in 10× Denhardt's solution, 5× SSC, 5 mM EDTA, 20 mM sodium phosphate, pH 7, 7% SDS, 100 µg/ml herring sperm DNA. The membranes were washed at 50° C., three times, 20 min. each, in 10× Denhardt's solution, 3× SSC, 70 mM sodium phosphate, 5% SDS, then once or twice at 60° C. in 1× SSC, 1% SDS.

All hybridization procedures were done using a Model 310 hybridization oven (Robbins Scientific, Sunnyvale, Calif., USA).

Each genomic insert was subcloned as fragments into plasmid vectors, ptz18r (Stratagene, La Jolla, Calif., USA) or pGEM-7 (Promega) for further gene mapping and direct sequence analysis.

The majority of the gene sequence—all exons, exon/intron junctions, and the major portion of intron sequence—was obtained using T7 DNA polymerase (Sequenase® brand, United States Biochemical, Cleveland, Ohio, USA) and [γ-$^{35}$S] dATP (DuPont, New England Nuclear). Several intron sequences were obtained by cycle sequencing using Taq polymerase, the Prism Dye Deoxyterminator kit, and the ABI 373A automated sequencing apparatus (Applied Biosystems, Foster City, Calif., USA). All sequences were determined according to the dideoxynucleotide termination method of Sanger et al. (1977), Proc. Natl. Acad. Sci. (USA) 74, 5463–5467 (the Sanger method).

Intron distances were determined by a combination of restriction mapping, PCR amplification, and direct sequencing procedures.

For genomic Southern blot hybridization, human genomic DNA was isolated from peripheral blood leukocytes separated from 50 ml of human blood drawn from a normal, healthy volunteer (See Poncz et al. (1982) Hemoglobin 6, 27–36). Ten μg of human genomic DNA was digested with various restriction endonucleases for 18 hr. at 37° C. The digests were separated through a 0.8% agarose gel by electrophoresis in Tris-borate-EDTA buffer at 30 volts for 18 hr., transferred to a nylon membrane, and hybridized with $^{32}$P-labeled PECAM-1 cDNA probes at 65° C. for at least 18 hr. in 5× Denhardt's solution, 6× SSC, 5 mM EDTA, 10 mM sodium phosphate, pH 7, 1% SDS, 100 μg/ml herring sperm DNA. Membranes were washed at 65° C. twice with 2× SSC, 0.1% SDS, then twice with 1× SSC, 0.1% SDS; each wash lasted 30 min. Washed membranes were exposed to Kodak XOMatAR or XRP film (Fotodyne, Milwaukee, Wis., USA) for one to two weeks in the presence of an amplifying screen.

Polymerase chain reaction was carried out as follows. One μg total human genomic DNA, 20 ng lambda phage DNA, or 2 ng plasmid DNA were routinely used as starting material for 100 μl PCR amplifications. PCR reactions were carried out in 10 mM Tris-HCl, pH 8, 1.5 mM MgCl$_2$, 50 mM KCl, 0.01% gelatin, and 0.2 mM of each dNTP (2'-deoxyribonucleoside triphosphate). Primers were added to a final concentration of 0.5 μM. PCR amplification was performed in a thermocycler (MJ Research, Inc. Watertown, Mass., USA) using the following protocol: (1) 3 min. DNA denaturation at 100° C., (2) 2 min. initial primer annealing at 55°–57° C., (3) heating to 72° C. followed by addition of 1 unit Taq polymerase (Perkin-Elmer Corp. Oakbrook, Ill., USA), (4) 1–5 min. extension at 72° C., (5) 1.0 min. denaturation at 96° C., (6) 1.0 min. primer annealing at 55°–57° C., (7) 30 cycles of steps 4–6, (8) final 7 min. extension, and (9) cooling to 4° C.

Primer Extension and 5'-Rapid Amplification of cDNA Ends (RACE) Analyses were carried out as follows. Human umbilical vein endothelial cells were harvested from umbilical cords and primary cultures were established as described by Newman et al. (III) (1986) J. Cell. Biol. 103, 81–86. Total RNA and PolyA mRNA was isolated according to previously published methods (Lyman et al. (1990) Blood 75, 2343–2348). Yeast tRNA was obtained from Life Technologies, Inc. (Gaithersburg, Md., USA). Primer extension reactions were conducted using the oligonucleotide of SEQ ID NO:12. The primer was labeled with [γ-$^{32}$P] ATP by kinasing and hybridized with either 15 μg of total RNA, 4 μg of polyA RNA, or 15 μg of yeast tRNA. Hybridization reactions were conducted at 56° C. in 125 mM Tris, pH 8.3 buffer containing 190 mM KCl, 7.5 mM MgCl$_2$. Extension reactions were carried out at 40° C. in 50 mM Tris, pH 8.3 buffer containing 75 mM KCl, 10 mM dithiothreitol (DTT), 3 mM MgCl$_2$, 0.5 mM of each dNTP, 0.05 mg/ml actinomycin D, 0.1 U/ml RNasin® brand ribonuclease inhibitor (Promega) and 0.2 U/ml MMLV reverse transcriptase. After extension, unprotected RNA was digested with RNaseH (10 U/ml), followed by ethanol precipitation of intact RNA-DNA hybrids. The products were electrophoresed through a 5% denaturing polyacrylamide gel and visualized by autoradiography. Sequencing reactions using the above primer and a genomic clone containing the 5'-end of the PECAM-1 gene (see below) were conducted using the Sanger method. 5'-RACE reactions were conducted according to the manufacturer's directions (Clontech, Inc.).

Identification of PECAM-1 mRNA splicing variants was carried out as follows. Total RNA was isolated from human umbilical vein endothelial cells by the method of Chomczynski and Sacchi (1987) Anal. Biochem. 162, 156–159 (1987). cDNA was generated from the isolated RNA with the antisense primer of SEQ ID NO:13 by reverse transcription at 37° C. using MMLV reverse transcriptase (Boehringer Mannheim Biochemicals). PCR amplification of cDNA employed a forward primer in exon 11 with the sequence SEQ ID NO:14 and an antisense primer spanning the exon 15/16 junction having the sequence SEQ ID NO:15. PCR products were separated by 2% agarose gel electrophoresis. On occasion, PCR products were excised directly from the gel, subcloned into a pGEM-5 plasmid vector (Promega) and sequenced as described above.

By a chromosomal localization analysis of human/hamster somatic cell hybrid clones, it was found that the genomic DNA for PECAM-1 (all forms) occurs in one copy on the long arm of human chromosome 17.

In order to determine the organization of the genomic DNA for human PECAM-1, two different lambda phage libraries and one P1 phagemid library were screened using a combination of PCR amplification (P1 phagemid library) and hybridization with PECAM-1-specific probes (phage libraries), as indicated supra. A total of six genomic clones, with inserts averaging approximately 15 kb (kilobase pairs) in size, were obtained.

Initial restriction mapping of these six clones revealed a genomic DNA of approximately 65 kb in size. The nucleotide sequence was determined for 30,127 base pairs of the PECAM-1 genomic DNA, including 561 bp (base pairs) 5' to the C at position 7 (the first base that is not part of the artifactual 5'-GAATTC EcoRI site) at the 5'-end of the previously reported PECAM-1 cDNA sequence (see FIG. 1 of the '554 Patent).

In order to localize the 5' end of genomic DNA coding for the PECAM-1 mRNA transcript (the beginning of exon 1) within this 561 bp segment, primer extension analysis was conducted. An antisense oligonucleotide with SEQ ID NO:12, a sequence complementary to that of a segment in the 5' region of the PECAM-1 mRNA, was used to prime reverse transcription of human umbilical vein endothelial cell (HUVEC), A549 lung carcinoma cell, and yeast RNAs. (The lung carcinoma cells and yeast cells do not express PECAM-1.) A specific band unique to HUVEC mRNA corresponding to the A at the nucleotide position immediately 3' to nucleotide 492 in SEQ ID NO:1 was obtained. This nucleotide is 204 bp upstream from the translation start site reported in FIG. 1 of the '554 Patent.

5' RACE PCR products derived from the 5' end of PECAM-1 mRNA were also generated; however, sequence analyses of several of these products showed three additional transcription start sites, all within eight nucleotides of the A immediately 3' of nucleotide 492 in SEQ ID NO:1. Localization of the transcription start site to this region is consistent with the findings of Zehnder et al., supra, who reported a cDNA clone containing a 207 bp 5' untranslated region. Thus, it appears that the PECAM-1 gene (the part of PECAM-1 genomic DNA that is transcribed) begins (and therefore the transcription start site of PECAM-1 genomic DNA is at) one of several closely spaced nucleotides, similar to the situation found for the genes for the vascular cell adhesion molecules E-selectin (Collins et al. (1991) J. Biol. Chem. 266, 2466–2473) and L-selectin (Ord et al. (1990) J. Biol. Chem. 265, 7760–7767).

The major organizational features of the PECAM-1 gene were found to be as follows. The gene is composed of 16 exons separated by introns ranging from 86 to greater than 12,000 base pairs in length. Exon 1, which corresponds to the 5' untranslated (UT) region of the PECAM-1 cDNA, also codes for mRNA that encodes most, but not all, of the signal peptide. Exon 2, which resides in close proximity to exon 1 on the gene and is only 27 bp in length, encodes the RNA that codes for the remainder of the signal peptide and the first three amino acids of the predicted N-terminus of the mature protein.

Thereafter, there is a direct correlation between exon/intron organization and the structure of the extracellular domain of the PECAM-1 protein. Similar to other members of the Ig superfamily, each of the six Ig homology domains (see FIG. 2 of the '554 Patent) corresponds to its own exon, numbered 3–8, which codes for the mRNA that encodes the homology domain.

The transmembrane segment (amino acids 575–593 in FIG. 1 of the '554 Patent) with its immediate flanking segments also corresponds to a separate exon, exon 9.

Unexpectedly, we found that the cytoplasmic tail of PECAM-1 is divided into seven distinct segments/regions, each of which corresponds to an exon of the PECAM gene. Thus, each of seven exons, exons 10–16, of the PECAM-1 gene, codes for mRNA that encodes a segment of the cytoplasmic tail. Exon 16 codes for the 3' UT (untranslated region) of the PECAM-1 mRNA transcript.

The nucleotide sequence for an additional 871 bp of the PECAM-1 genomic DNA that is 3' to the triplet of the gene that codes for the translation stop codon was also determined. In this 871 bp segment, a consensus primary 5'-AATAAA polyadenylation sequence was not found. However, two secondary consensus sequences, 5'-GATAAA and 5'-AATACA, were noted after the triplet coding for the stop codon.

Alternative splicing (sometimes referred to herein as "differential" splicing) of the transcript of the PECAM-1 gene was discovered. Each intron begins with the consensus splice-donor sequence "GT" and ends with the consensus "AG" splice-acceptor sequence. Interestingly, all exons with the exceptions of exon 10 and 15 terminate with the first base of triplet that encodes a codon, thus having the classification of "phase 1" exons (Sharp (1981) Cell 23, 643–646). In particular, five of seven exons that correspond to the transmembrane and cytoplasmic domains (exons 9–15), as well as exon 8, are of the phase 1 class, leading to the possibility of in-frame alternative splicing events yielding PECAM-1 isoforms that are soluble because of lack of a transmembrane domain or that differ in the sequence of the cytoplasmic tail.

In order to examine whether such isoforms might be generated within the cell, HUVEC mRNA was subjected to RT-PCR amplification of a region coded for by exons 11–16 using a primer with the sequence of SEQ ID NO:14 and a primer with the sequence of SEQ ID NO:15. Two PCR products were isolated by agarose gel electrophoresis: a 260 bp major product, corresponding to a full-length segment containing all of exons 12–15, part of exon 11, and part of exon 16, and a minor 200 bp product that hybridized with a full-length PECAM-1 cDNA probe. When the minor, mRNA-derived PCR product was subcloned and sequenced, it was found to be the same as the full length product except that is was missing exon 14. Thus, the mRNA corresponding to this minor product encodes a PECAM-1Δ14 isoform.

A "PECAM-1Δx isoform" is the isoform that has the sequence of amino acids that results from translation of the mRNA that is the same as an mRNA that is translated to make a full-length PECAM-1 except that the mRNA that is translated to make the isoform lacks the mRNA segment corresponding to exon x of the gene for the PECAM-1. Similarly, a "PECAM-1Δx,y, . . . z isoform" is the isoform that has the sequence of amino acids that results from translation of the mRNA that is the same as an mRNA that is translated to make a full-length PECAM-1 except that the mRNA that is translated to make the isoform lacks the mRNA segments corresponding to exons x, y, . . . and z of the gene for the PECAM-1.

By examination of the exon organization of the PECAM-1 gene, it has been determined that the soluble form of PECAM-1 identified by Goldberger et al., supra, is a PECAM-1 isoform encoded by an mRNA missing the segment coded by exon 9 of the genomic DNA (i.e., a PECAM-1Δ9 isoform). The missing segment in this mRNA, corresponding to exon 9, includes a subsegment which encodes the transmembrane domain, amino acids 575–593 of PECAM-1, as shown in FIG. 1 of the '554 Patent).

A cDNA has been found that differs from the cDNA for which the sequence is reported in FIG. 1 of the '554 Patent substantially only in lacking the 63 base pair segment corresponding to bases 2186–2248 shown in that FIG. 1. This segment corresponds exactly to exon 13 of the PECAM-1 gene for which the cDNA sequence is provided in FIG. 1 of the '554 Patent. Thus, a PECAM-1Δ13 isoform has been found.

Because exons 12, 13 and 14 are all phase 1 exons, splicing out of the PECAM-1-encoding mRNA the segment coded for by exon 13 results in the precise deletion of 21 amino acids without changing the reading frame of the mRNA encoding the remainder of the cytoplasmic tail. The amino acid segment corresponding to exon 13 contains 4 of the 12 serine residues found in the cytoplasmic domain of PECAM-1 and so, when present, is likely to serve as a site for post-translational phosphorylation and cytoskeletal association of PECAM-1. Thus, the PECAM-1Δ13 isoform should have differential ability, in comparison with PECAM-1 itself or other isoforms thereof, to become phosphorylated and associate with the cytoskeleton.

Others have recently isolated and characterized a murine PECAM-1 isoform, a murine PECAM-1Δ12,15, from developing cardiac endothelium. This isoform has an amino acid sequence that differ from that of the full length, mature molecule because it is encoded by an RNA that differs from an RNA that encodes the full-length molecule in lacking segments corresponding to exons 12 and 15 of the gene for the murine PECAM-1.

Thus, it would appear that the highly divided exon/intron organization of the PECAM-1 gene in the region corresponding to the cytoplasmic tail is actively used by the cells in which PECAM-1 is made for the generation of multiple PECAM-1 isoforms.

Surprisingly, the multiple-exon, mosaic structure of the PECAM-1 genomic DNA extends to the cytoplasmic region. Unlike the genes for the homologous proteins, ICAM-1 and VCAM-1, which combine the coding regions for the transmembrane and cytoplasmic domains into a single exon, the cytoplasmic tail of PECAM-1 has been found to be encoded by an RNA coded for by seven separate, small exons, each of which appears to represent a domain with a discrete function.

EXAMPLE 2

In this example, a method is provided for eliminating from a cDNA for a PECAM-1, or an isoform thereof, a particular, pre-determined segment. In this example, the method is used to eliminate the cDNA segment that corresponds to bases 44–100 of exon 9 shown in SEQ ID NO:4. This cDNA segment codes for the segment of PECAM-1-encoding mRNA that encodes the "transmembrane domain". A PECAM-1 isoform expressed from a cDNA lacking this segment is soluble.

The skilled could easily adapt the method described here to eliminate, from a cDNA segment coding for an mRNA encoding a full-length PECAM-1 or an isoform thereof, the segment corresponding to any one or more of exons 9–15. The information required to so adapt the method is information provided herein on the sequences of the exons in PECAM-1 genomic DNA (and, therefore, exon boundaries in PECAM-1 cDNAs) and information readily available in the art, including that on cDNA sequences for full-length PECAM-1's (e.g., the '554 Patent; Stockinger et al., supra; and Zehnder et al., supra), sequences of restriction enzyme recognition and cleavage sites, and sequences of many suitable cloning vectors.

The technique described here is based on that described by Kahn (1990) Technique—A Journal of Methods in Cell and Molecular Biology 2, 27–30.

The PECAM-1 cDNA, whose sequence is illustrated in FIG. 1 of the '554 Patent, was held in a vector between two EcoRI sites. Indeed, the 5'-GAATT shown in that Figure at the 5'-end of the cDNA is part of an EcoRI site and an artifact of the method of preparing the cDNA library, from which the cDNA was prepared, and isolating the cDNA from the library.

A PECAM-1 cDNA, with the sequence shown in FIG. 1 of the '554 Patent, was converted by site-directed mutagenesis to a more preferred cDNA, that is conveniently without the two internal EcoRI sites in the cDNA with the sequence in that FIG. 1. The sequence of the EcoRI site at positions 684–689 in that Figure was converted to 5'-GAACTC. The sequence of the site at positions 715–720 in that Figure was converted to 5'-GAGTTC. The two base changes are silent. The resulting cDNA is referred to herein as "the FIG. 1-EcoRI-less" PECAM-1 cDNA.

The FIG. 1-EcoRI-less PECAM-1 cDNA was cloned into the EcoRI site of a pGEM-7 plasmid vector (Promega), where it is conveniently held for production, modification, and excision with EcoRI for transfer to other vectors, including expression vectors, or other purposes. Many other vectors available in the art, rather than a pGEM-7 vector, would be suitable as well for these purposes.

A 343 base pair segment, bases 1602–1944 of the sequence shown in FIG. 1 of the '554 Patent, of the FIG. 1-EcoRI-less PECAM-1 cDNA in the pGEM-7 vector was amplified by PCR using a primer with the sequence of SEQ ID NO:16 and a primer with the sequence of SEQ ID NO:17. The product of the amplification was a 361 base pair segment, referred to herein as "Segment A," which consisted of the 343 base pair segment at one end and a 18 base pair segment at the other end with the sequence of bases 2002–2019 as shown in FIG. 1 of the '554 Patent. Segment A was isolated from the reaction mixture.

Note that the cDNA segment with the sequence of bases 1945–2001 as shown in FIG. 1 of the '554 Patent corresponds to the segment of exon 9 with the sequence of bases 44–100 shown in SEQ ID NO:4.

A 481 base pair segment, bases 2002–2482 of the sequence shown in FIG. 1 of the '554 Patent, of the FIG. 1-EcoRI-less PECAM-1 cDNA in the pGEM-7 vector was amplified by PCR using a primer with the sequence of SEQ ID NO:18 and a primer with the sequence of SEQ ID NO:19. The product of the amplification was a 497 base pair segment, referred to herein as "Segment B," which consisted of the 481 base pair segment at one end and at the other end a 16 base pair segment with the sequence of bases 1929–1944 as shown in FIG. 1 of the '554 Patent. Segment B was isolated from the reaction mixture.

Note that the sequence of a 34 base pair segment at one end of Segment A is the same as that of a 34 base pair segment at one end of Segment B. Consequently each strand of Segment A can prime a primer extension reaction on one of the strands of Segment B as a template and each strand of Segment B can prime a primer extension reaction on one of the strands of Segment A as a template.

A PCR reaction was then carried out with the combination of Segment A, Segment B, a primer with the sequence of SEQ ID NO:20, and a primer with the sequence of SEQ ID NO:21. The major product of this reaction was a 533 base pair segment, referred to here as "Segment C," with a subsegment at one end with the sequence of bases 1754–1944 as shown in FIG. 1 of the '554 Patent and a subsegment at the other end with the sequence of bases 2002–2343 as shown in that FIG. 1.

Segment C has an NheI site (5'-GCTAGC, with cleavage between the G and the C at the 5'-end) as the subsegment corresponding to bases 1825–1830 shown in FIG. 1 of the '554 Patent and a BglII site (5'-AGATCT, with cleavage between the A and the G at the 5'-end) as the subsegment corresponding to bases 2247–2252 shown in FIG. 1 of the '554 Patent.

Segment C was cut with NheI and BglII and the approximately 369 bp fragment was isolated.

Full length FIG. 1-EcoRI-less PECAM-1 cDNA in the pGEM-7 vector was also cut with NheI and BglII and the larger fragment isolated. Note that the pGEM-7 vector itself has no sites for NheI and BglII.

The 369 base pair fragment of Segment C was then ligated into the larger fragment from the NheI/BglII-cleavage of the pGEM-7 vector with the FIG. 1-EcoRI-less PECAM-1 cDNA. The resulting vector had cDNA for a soluble PECAM-1 isoform which had the entire amino acid sequence shown in FIG. 1 of the '554 Patent except the amino acids of the "transmembrane domain," amino acids 575–593 as shown in that Figure or, alternatively, amino acids 9–27 as shown in SEQ ID NO:4.

---

We claim:

1. An isolated DNA molecule consisting of a nucleotide sequence selected from the group consisting of SEQ ID NO:1 and SEQ ID NO:2, wherein said DNA molecule is a human platelet-endothelial cell adhesion molecule-1 (PECAM-1) promoter.

2. An expression vector comprising the promoter of claim 1.

3. The expression vector of claim 2, further comprising a second DNA molecule that encodes a polypeptide, wherein said promoter is operably linked to said second DNA molecule.

4. An isolated DNA molecule consisting of a nucleotide sequence that is a subsegment of the nucleotide sequence of SEQ ID NO:1, wherein said DNA molecule is capable of stimulating transcription within a mammalian cell of the vasculature at a rate that is at least 10% of the transcription rate stimulated by a DNA molecule having the nucleotide sequence of SEQ ID No:1 under comparable conditions.

\* \* \* \* \*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 492 base pairs
( B ) TYPE: nucleic acid
( C ) STRANDEDNESS: double
( D ) TOPOLOGY: linear ( x i ) SEQUENCE DESCRIPTION: SEQ ID NO:1:

-continued

```
TCTTTTGGTT TTGCTATTGC TTAAGCTAGC CTACGCCAAG GGTGCTCTTT GCCCCCTACT       60

TCCTCTGCTA TTCTCGCCTC AGTTCCGCTG CATTCCAAGC TCAGCCTGCC CCAGCAGCAG      120

GTCTCTTTGA CAAACCTGCA ATTTGGGGA  AAAGTCAGCC CAAGAAAGGC AGGGGGCCCA      180

GACTTATGCT GTGTGGCAAA AGCCCTCTTT GATGGGGCAA GGGTAGGACT GGAAAAGCAG      240

AGAGATCTTT CTGGATGTCC TGGGAGAGCA GCCCTTTGGG TGGTGGGTGG AGGCTGGAGG      300

CAGGGAGGAA TCCCCTCACA GTGAGAAGGG CCCCCAAACC CAGGCGAGAC AGAGGGAGGG      360

TCAAGAACGC CAAGGCAAAT GTCACTTGTG CCTTGTTTTT TCCCTAAAGA AACTAAACAA      420

AGCGGCCGCG TTCGGTGGCC CCTCAGGAAG GCCGGTCATT TCCTGAGGAG ATATCAGGCC      480

AGCCCAGGCC CC                                                          492
```

( 2 ) INFORMATION FOR SEQ ID NO:2:

( i ) SEQUENCE CHARACTERISTICS:
        ( A ) LENGTH: 234 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CCTGGGAGAG CAGCCCTTTG GGTGGTGGGT GGAGGCTGGA GGCAGGGAGG AATCCCCTCA       60

CAGTGAGAAG GGCCCCCAAA CCCAGGCGAG ACAGAGGGAG GGTCAAGAAC GCCAAGGCAA      120

ATGTCACTTG TGCCTTGTTT TTTCCCTAAA GAAACTAAAC AAAGCGGCCG CGTTCGGTGG      180

CCCCTCAGGA AGGCCGGTCA TTTCCTGAGG AGATATCAGG CCAGCCCAGG CCCC            234
```

( 2 ) INFORMATION FOR SEQ ID NO:3:

( i ) SEQUENCE CHARACTERISTICS:
        ( A ) LENGTH: 308 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
CC  CCG GTG GAT GAG GTC CAG ATT TCT ATC CTG TCA AGT AAG GTG GTG        47
Ala Pro Val Asp Glu Val Gln Ile Ser Ile Leu Ser Ser Lys Val Val
            5               10              15

GAG TCT GGA GAG GAC ATT GTG CTG CAA TGT GCT GTG AAT GAA GGA TCT        95
Glu Ser Gly Glu Asp Ile Val Leu Gln Cys Ala Val Asn Glu Gly Ser
        20              25              30

GGT CCC ATC ACC TAT AAG TTT TAC AGA GAA AAA GAG GGC AAA CCC TTC       143
Gly Pro Ile Thr Tyr Lys Phe Tyr Arg Glu Lys Glu Gly Lys Pro Phe
    35              40              45

TAT CAA ATG ACC TCA AAT GCC ACC CAG GCA TTT TGG ACC AAG CAG AAG       191
Tyr Gln Met Thr Ser Asn Ala Thr Gln Ala Phe Trp Thr Lys Gln Lys
50              55              60

GCT AAC AAG GAA CAG GAG GGA GAG TAT TAC TGC ACA GCC TTC AAC AGA       239
Ala Asn Lys Glu Gln Glu Gly Glu Tyr Tyr Cys Thr Ala Phe Asn Arg
65              70              75              80

GCC AAC CAC GCC TCC AGT GTC CCC AGA AGC AAA ATA CTG ACA GTC AGA       287
Ala Asn His Ala Ser Ser Val Pro Arg Ser Lys Ile Leu Thr Val Arg
            85              90              95

G GTGAGTCAGG GTCTCCATAG                                                308
```

( 2 ) INFORMATION FOR SEQ ID NO:4:

( i ) SEQUENCE CHARACTERISTICS:
        ( A ) LENGTH: 148 base pairs
        ( B ) TYPE: nucleic acid ( C ) STRANDEDNESS: double
( D ) TOPOLOGY: linear ( x i ) SEQUENCE DESCRIPTION: SEQ ID NO:4:

| TTGTTTTGTT | TTGTTTTCAG | TC ATT | CTT | GCC | CCA | TGG | AAG | AAA | GGA | CTT | ATT | 52 |
| | | Val Ile | Leu | Ala | Pro | Trp | Lys | Lys | Gly | Leu | Ile | |
| | | | | | 5 | | | | | | 10 | |

| GCA | GTG | GTT | ATC | ATC | GGA | GTG | ATC | ATT | GCT | CTC | TTG | ATC | ATT | GCG | GCC | 100 |
| Ala | Val | Val | Ile | Ile | Gly | Val | Ile | Ile | Ala | Leu | Leu | Ile | Ile | Ala | Ala | |
| | | | 15 | | | | 20 | | | | | 25 | | | | |

| AAA | TGT | TAT | TTT | CTG | AGG | AAA | GCC | AAG | G GTGAGCATAG TTCTTTCCTT | 148 |
| Lys | Cys | Tyr | Phe | Leu | Arg | Lys | Ala | Lys | | |
| | | | 30 | | | | 35 | | | |

( 2 ) INFORMATION FOR SEQ ID NO:5:

( i ) SEQUENCE CHARACTERISTICS:
( A ) LENGTH: 68 base pairs
( B ) TYPE: nucleic acid
( C ) STRANDEDNESS: double
( D ) TOPOLOGY: linear ( x i ) SEQUENCE DESCRIPTION: SEQ ID NO:5:

| TTCGTTTTCT | GTTTTAAAG | CC | AAG | CAG | ATG | CCA | GTG | GAA | ATG | TCC | AG | 48 |
| | | | Ala | Lys | Gln | Met | Pro | Val | Glu | Met | Ser | Arg | |
| | | | | | | | 5 | | | | | 10 | |

GTGAGTGTAT TTGTAAGAAG                                                                68

( 2 ) INFORMATION FOR SEQ ID NO:6:

( i ) SEQUENCE CHARACTERISTICS:
( A ) LENGTH: 114 base pairs
( B ) TYPE: nucleic acid
( C ) STRANDEDNESS: double
( D ) TOPOLOGY: linear ( x i ) SEQUENCE DESCRIPTION: SEQ ID NO:6:

| TTTTATATTT | CATTTTAAAG | G | CCA | GCA | GTA | CCA | CTT | CTG | AAC | TCC | AAC | AAC | 51 |
| | | | Pro | Ala | Val | Pro | Leu | Leu | Asn | Ser | Asn | Asn | |
| | | | | | | | | 5 | | | | 10 | |

| GAG | AAA | ATG | TCA | GAT | CCC | AAT | ATG | GAA | GCT | AAC | AGT | CAT | TAC | G | 94 |
| Glu | Lys | Met | Ser | Asp | Pro | Asn | Met | Glu | Ala | Asn | Ser | His | Tyr | | |
| | | | 15 | | | | | 20 | | | | | | | |

GTAAAGTCAT GTTCTCCTGC                                                                114

( 2 ) INFORMATION FOR SEQ ID NO:7:

( i ) SEQUENCE CHARACTERISTICS:
( A ) LENGTH: 94 base pairs
( B ) TYPE: nucleic acid
( C ) STRANDEDNESS: double
( D ) TOPOLOGY: linear ( x i ) SEQUENCE DESCRIPTION: SEQ ID NO:7:

| AATTGTTATT | TTTCAACTAG | GT | CAC | AAT | GAC | GAT | GTC | AGA | AAC | CAT | GCA | ATG | 52 |
| | | | Gly | His | Asn | Asp | Asp | Val | Arg | Asn | His | Ala | Met | |
| | | | | | | | 5 | | | | | 10 | |

| AAA | CCA | ATA | AAT | GAT | AAT | AAA | G GTAATTATCT AATTACATGT | 94 |
| Lys | Pro | Ile | Asn | Asp | Asn | Lys | | |
| | | | 15 | | | | | |

( 2 ) INFORMATION FOR SEQ ID NO:8:

( i ) SEQUENCE CHARACTERISTICS:
( A ) LENGTH: 103 base pairs
( B ) TYPE: nucleic acid ( C ) STRANDEDNESS: double
( D ) TOPOLOGY: linear ( x i ) SEQUENCE DESCRIPTION: SEQ ID NO:8:

```
TCTGTGGTTT CTTTAGGCAG AG CCT CTG AAC TCA GAC GTG CAG TAC ACG GAA      52
                         Glu Pro Leu Asn Ser Asp Val Gln Tyr Thr Glu
                                        5                          10

GTT CAA GTG TCC TCA GCT GAG TCT CAC AAA G GTAAGTGCCA CTCGAGTGAG       103
Val Gln Val Ser Ser Ala Glu Ser His Lys
 15                              20
```

( 2 ) INFORMATION FOR SEQ ID NO:9:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

```
ATGCCTGGTC CTTTTCCAG AT CTA GGA AAG AAG GAC ACA GAG ACA GTG TAC      52
                        Asp Leu Gly Lys Lys Asp Thr Glu Thr Val Tyr
                                        5                          10

AGT GAA GTC CGG AAA GCT GTC CCT G GTGAGTGAGG GTCTCCAGTG              97
Ser Glu Val Arg Lys Ala Val Pro
                 15
```

( 2 ) INFORMATION FOR SEQ ID NO:10:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

```
TGTCATCCTT TGTTTTGTAG AT GCC GTG GAA AGC AGA TAC TCT GTAAGTACAC      53
                         Asp Ala Val Glu Ser Arg Tyr Ser
                                          5

ATTTCATATA                                                           63
```

( 2 ) INFORMATION FOR SEQ ID NO:11:

( i ) SEQUENCE CHARACTERISTICS:
        ( A ) LENGTH: 921 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:11:

```
CTTGTTTCTT GTCGCTACAG AGA ACG GAA GGC TCC CTT GAT GGA ACT TAG        50
                      Arg Thr Glu Gly Ser Leu Asp Gly Thr
                                      5

ACAGCAAGGC CAGATGCACA TCCCTGGAAG GACATCCATG TTCCGAGAAG AACAGATGAT    110
CCCTGTATTT CAAGACCTCT GTGCACTTAT TTATGAACCT GCCCTGCTCC CACAGAACAC    170
AGCAATTCCT CAGGCTAAGC TGCCGGTTCT TAAATCCATC CTGCTAAGTT AATGTTGGGT    230
AGAAAGAGAT ACAGAGGGGC TGTTGAATTT CCCACATACC CTCCTTCCAC CAAGTTGGAA    290
CATCCTTGGA AATTGGGAAG AGCACAAGAG GAGATCCAGG GCAAGGCCAT TGGGATATTC    350
TGAAACTTGA ATATTTTGTT TTGTGCAGAG ATAAAGACCT TTTCCATGCA CCCTCATACA    410
CAGAAACCAA TTTTCTTTTT TATACTCAAT CATTTCTAGC GCATGGCCTG GTTAGAGGCT    470
GGTTTTTTCT CTTTTCCTTT GGTCCTTCAA AGGCTTGTAG TTTGGGTAG TCCTTGTTCT     530
```

```
TTGGAAATAC ACAGTGCTGA CCAGACAGCC TCCCCCTGTC CCCTCTATGA CCTCGCCCTC      590

CACAAATGGG AAAACCAGAC TACTTGGGAG CACCGCCTGT GAAATACCAA CCTGAAGACA      650

CGGTTCATTC AGGCAACGCA CAAAACAGAA AATGAAGGTG GAACAAGCAC ATATGTTCTT      710

CAACTGTTTT TGTCTACACT CTTTCTCTTT TCCTCTACAT GCTGAAGGCT GAAAGACAGG     770

AAAGATGGTG CCATCAGCAA ATATTATTCT TAATTGAAAA CTTGAAATGT GTATGTTTCT      830

TACTAATTTT TAAAAATGTA TTCCTTGCCA GGGCAGGCAA GGTCGTCACG CCTGTAATCC      890

CAGCACTTCA GGAGGCTGAG GTGGGCGGAT C                                    921
```

( 2 ) INFORMATION FOR SEQ ID NO:12:

( i ) SEQUENCE CHARACTERISTICS:
       ( A ) LENGTH: 42 bases
       ( B ) TYPE: nucleic acid
       ( C ) STRANDEDNESS: single
       ( D ) TOPOLOGY: linear ( x i ) SEQUENCE DESCRIPTION: SEQ ID NO:12:

```
CCTGAGAGTG AAGACTGCAG GCACAGTTAG TTCTGCCTTC GG                         42
```

( 2 ) INFORMATION FOR SEQ ID NO:13:

( i ) SEQUENCE CHARACTERISTICS:
       ( A ) LENGTH: 18 bases
       ( B ) TYPE: nucleic acid
       ( C ) STRANDEDNESS: single
       ( D ) TOPOLOGY: linear ( x i ) SEQUENCE DESCRIPTION: SEQ ID NO:13:

```
TGCTGTGTTC TGTGGGAG                                                    18
```

( 2 ) INFORMATION FOR SEQ ID NO:14:

( i ) SEQUENCE CHARACTERISTICS:
       ( A ) LENGTH: 18 bases
       ( B ) TYPE: nucleic acid
       ( C ) STRANDEDNESS: single
       ( D ) TOPOLOGY: linear ( x i ) SEQUENCE DESCRIPTION: SEQ ID NO:14:

```
CAACGAGAAA ATGTCAGA                                                    18
```

( 2 ) INFORMATION FOR SEQ ID NO:15:

( i ) SEQUENCE CHARACTERISTICS:
       ( A ) LENGTH: 20 bases
       ( B ) TYPE: nucleic acid
       ( C ) STRANDEDNESS: single
       ( D ) TOPOLOGY: linear ( x i ) SEQUENCE DESCRIPTION: SEQ ID NO:15:

```
GGAGCCTTCC GTTCTAGAGT                                                  20
```

( 2 ) INFORMATION FOR SEQ ID NO:16:

( i ) SEQUENCE CHARACTERISTICS:
       ( A ) LENGTH: 20 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:16:

```
GTTAAGTGAG GTTCTGAGGG                                                  20
```

-continued ( 2 ) INFORMATION FOR SEQ ID NO:17:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ACGGGGTACC   TTCTTTTTA   CAATAAAAGA   CTCC                     34
```

( 2 ) INFORMATION FOR SEQ ID NO:18:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
TGCCCCATGG   AAGAAAAAAT   GTTATTTTCT   GAGG                     34
```

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
TGCTGTGTTC   TGTGGGAG                                           18
```

( 2 ) INFORMATION FOR SEQ ID NO:20:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
GAGAAAAAGA   GGGCAAACCC                                         20
```

( 2 ) INFORMATION FOR SEQ ID NO:21:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GGAGCCTTCC   GTTCTAGAGT                                         20
```